(12) United States Patent
Chang (10) Patent No.: US 12,343,129 B2
(45) Date of Patent: Jul. 1, 2025

(54) FMCW RADAR DEVICE AND METHOD FOR DETECTING VITAL INFORMATION AND HUMIDITY

(71) Applicant: Wistron Corporation, New Taipei (TW)

(72) Inventor: Yao-Tsung Chang, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 469 days.

(21) Appl. No.: 17/720,525

(22) Filed: Apr. 14, 2022

(65) Prior Publication Data

US 2023/0240550 A1 Aug. 3, 2023

(30) Foreign Application Priority Data

Jan. 28, 2022 (TW) .................................. 111104101
Jan. 28, 2022 (TW) .................................. 111104102

(51) Int. Cl.
*A61B 5/0507* (2021.01)
*A61F 13/42* (2006.01)
*G01S 7/35* (2006.01)
*G01S 7/41* (2006.01)
*G01S 13/34* (2006.01)

(52) U.S. Cl.
CPC ............ *A61B 5/0507* (2013.01); *A61F 13/42* (2013.01); *G01S 7/356* (2021.05); *G01S 7/412* (2013.01);

(Continued)

(58) Field of Classification Search
CPC .... A61F 13/42; A61F 2013/424; G01S 13/34; G01S 13/536; G01S 13/74; G01S 13/75; G01S 13/86; G01S 13/88; G01S 7/03; G01S 7/356; G01S 7/412; G01S 7/415; A61B 2503/045; A61B 2503/08;
(Continued)

(56) References Cited

U.S. PATENT DOCUMENTS 10,271,766 B1  4/2019  Parker, Jr. et al.
2005/0040832 A1*  2/2005  Steele .................... G01N 22/04
                                                324/640

(Continued)

FOREIGN PATENT DOCUMENTS

CN   101489478 A   7/2009
CN   105476602 A   4/2016
(Continued)

OTHER PUBLICATIONS

Examination report dated Jan. 16, 2023, listed in related Taiwan patent application No. 111104102.
(Continued)

*Primary Examiner* — Mark D Remaly
(74) *Attorney, Agent, or Firm* — McClure, Qualey & Rodack, LLP (57) ABSTRACT

A method for detecting vital information and humidity by using a frequency-modulated continuous wave (FMCW) radar device is provided, including: transmitting an incident radar signal to a field, detects a reflected radar signal reflected by a to-be-measured object and a reflected radar signal reflected by a humidity sensor tag, so as to obtain vital information of the to-be-measured object and humidity information detected by the humidity sensor tag.

10 Claims, 11 Drawing Sheets

(52) U.S. Cl.
CPC .............. *G01S 7/415* (2013.01); *G01S 13/34* (2013.01); *A61B 2562/029* (2013.01); *A61F 2013/424* (2013.01)

(58) Field of Classification Search
CPC ...... A61B 2562/0228; A61B 2562/029; A61B 5/0507; A61B 5/7225; A61B 5/7228
See application file for complete search history.

(56) References Cited

U.S. PATENT DOCUMENTS

| | | |
|---|---|---|
| 2007/0100666 A1 | 5/2007 | Stivoric |
| 2010/0090802 A1 | 4/2010 | Nilsson et al. |
| 2013/0001422 A1 | 1/2013 | Lavon et al. |
| 2014/0163343 A1 | 6/2014 | Heneghan et al. |
| 2017/0173262 A1 | 6/2017 | Veltz |
| 2018/0256030 A1 | 9/2018 | Lee et al. |
| 2018/0360329 A1* | 12/2018 | Chang .................... A61B 8/488 |
| 2019/0215672 A1 | 7/2019 | Orris |
| 2019/0365244 A1 | 12/2019 | Horng et al. |
| 2020/0261278 A1 | 8/2020 | Kawai et al. |
| 2020/0286605 A1 | 9/2020 | Chang |
| 2021/0302558 A1 | 9/2021 | Peng |

FOREIGN PATENT DOCUMENTS

| | | |
|---|---|---|
| CN | 106580277 A | 4/2017 |
| CN | 112014837 A | 12/2020 |
| TW | M569679 U | 11/2018 |

OTHER PUBLICATIONS eESR dated Sep. 27, 2022, listed in related European patent application No. 22 168 126.5.
Office Action dated Apr. 9, 2024, listed in related U.S. Appl. No. 17/696,999 (copy not provided).
Yasari. "Detecting Synthetic Urine Leakage Using MmWave Radar," Blekinge Institute of Technology, Sep. 2021 (Year: 2021).
Tajin et al. "Passive RFID-based Diaper Moisture Sensor," DOI 10.1109/JSEN.2020.3021395, IEEE Sensors Journal (Year: 2020).
"A Low-Profile Ultra-Wideband Directional Antenna" 2017.
"High-Gain Antipodal Vivaldi Antenna Surrounded by Dielectric for Wideband Applications"; Aug. 2018.
"R&S® NRPM Over-The-Air (OTA) Power Measurement Solution" 2017.
"On-Body Humidity Sensing Antenna with Polyimide for BAN Applications over 5G Networks" 2020.
Examination report dated Jul. 18, 2024, listed in related U.S. Appl. No. 17/696,999.
Examination report dated Nov. 27, 2024, listed in related U.S. Appl. No. 17/696,999.
Examination report dated Jul. 31, 2023, listed in related Taiwan patent application No. 111104101.
Examination report dated Feb. 24, 2023 listed in related Taiwan patent application No. 111104101.
Examination report dated Mar. 24, 2025, listed in related U.S. Appl. No. 17/696,999 (copy not provided).

* cited by examiner

FMCW RADAR DEVICE AND METHOD FOR DETECTING VITAL INFORMATION AND HUMIDITY

CROSS-REFERENCES TO RELATED APPLICATIONS

This non-provisional application claims priority under 35 U.S.C. § 119(a) to Patent Application No. 111104101 filed in Taiwan, R.O.C. on Jan. 28, 2022 and Patent Application No. 111104102 filed in Taiwan, R.O.C. on Jan. 28, 2022, the entire contents of which are hereby incorporated by reference.

BACKGROUND

Technical Field

The present invention relates to a radar signal processing technology, and in particular, to a frequency-modulated continuous wave (FMCW) radar device and detection of vital information and humidity.

Related Art

At present, although there are physiological information detection radars used to detect breathing and heartbeat, in applications such as patient care, long-term care for the elderly, and infant care, for patients, the elderly, and infants who need to wear diapers, the humidity state of their diapers cannot be detected at the same time, and there are still defects.

SUMMARY

According to some embodiments, a method for detecting vital information and humidity is provided, including: transmitting an incident radar signal to a field, and receiving a reflected radar signal corresponding to the field, where the incident radar signal includes a plurality of chirp signals; demodulating the reflected radar signal according to the incident radar signal to obtain a first intermediate frequency signal; demodulating the reflected radar signal according to the frequency-multiplied incident radar signal to obtain a second intermediate frequency signal; processing the first intermediate frequency signal to obtain vital information of a to-be-measured object; and obtaining humidity information according to an energy peak time point of the second intermediate frequency signal.

According to some embodiments, an FMCW radar device is provided, including: a transmitting unit, a receiving unit, a first demodulation unit, a second demodulation unit, and a processing unit. The transmitting unit is configured to transmit an incident radar signal to a field, where the incident radar signal includes a plurality of chirp signals. The receiving unit is configured to receive a reflected radar signal corresponding to the field. The first demodulation unit is coupled to the transmitting unit and the receiving unit, and is configured to obtain a first intermediate frequency signal according to the reflected radar signal and the incident radar signal through demodulation. The second demodulation unit is coupled to the transmitting unit and the receiving unit, and is configured to obtain a second intermediate frequency signal according to the reflected radar signal and the frequency-multiplied incident radar signal through demodulation. The processing unit is coupled to the transmitting unit, the receiving unit, and the demodulation unit, and is configured to process the first intermediate frequency signal to obtain vital information of a to-be-measured object, and obtain humidity information according to an energy peak time point of the second intermediate frequency signal.

According to some embodiments, an FMCW radar device is provided, including: a transmitting unit, a receiving unit, a first demodulation unit, a second demodulation unit, and a processing unit. The transmitting unit is configured to transmit two incident radar signals having a first frequency modulation frequency band and a second frequency modulation frequency band respectively to a field, where the two incident radar signals include a plurality of chirp signals. The receiving unit is configured to receive a reflected radar signal corresponding to the field. The first demodulation unit is coupled to the transmitting unit and the receiving unit, and is configured to receive the incident radar signal having the first frequency modulation frequency band, and obtain a first intermediate frequency signal according to the reflected radar signal and the incident radar signal having the first frequency modulation frequency band through demodulation. The second demodulation unit is coupled to the transmitting unit and the receiving unit, is configured to receive the incident radar signal having the second frequency modulation frequency band, and obtain a second intermediate frequency signal according to the reflected radar signal and the incident radar signal having the second frequency modulation frequency band through demodulation. The processing unit is coupled to the transmitting unit, the receiving unit, and the demodulation unit, and is configured to process the first intermediate frequency signal to obtain vital information of a to-be-measured object, and obtain humidity information according to an energy peak time point of the second intermediate frequency signal.

In summary, the FMCW radar device and the method for detecting vital information and humidity according to some embodiments can measure the vital information and humidity at the same time, thereby saving device space and the hardware costs.

DETAILED DESCRIPTION

The term "couple" used in the specification means that two or more elements are in direct physical or electrical contact with each other, or are in indirect physical or electrical contact with each other.

Figure 1:
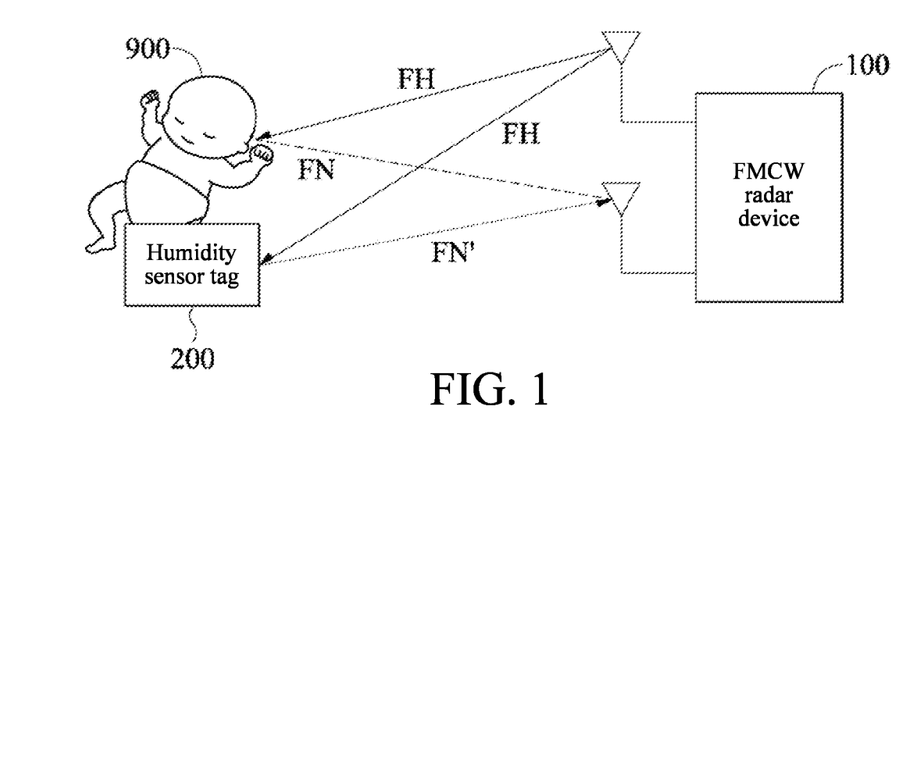
FIG. 1 is a schematic diagram of a usage state of an FMCW radar device according to some embodiments.

FIG. 1 is a schematic diagram of a usage state of a frequency-modulated continuous wave (FMCW) radar device 100 according to some embodiments. The FMCW radar device 100 transmits a radar signal (referred to as an "incident radar signal FH" hereinafter). The incident radar signal FH is transmitted to a field, and is reflected back to the FMCW radar device 100 by a to-be-measured object 900, a humidity sensor tag 200, an environment, or the like. A radar signal reflected by the to-be-measured object 900 is referred to as a "reflected radar signal FN" hereinafter, and a radar signal reflected by the humidity sensor tag 200 is referred to as a "reflected radar signal FN'".

Figure 2:
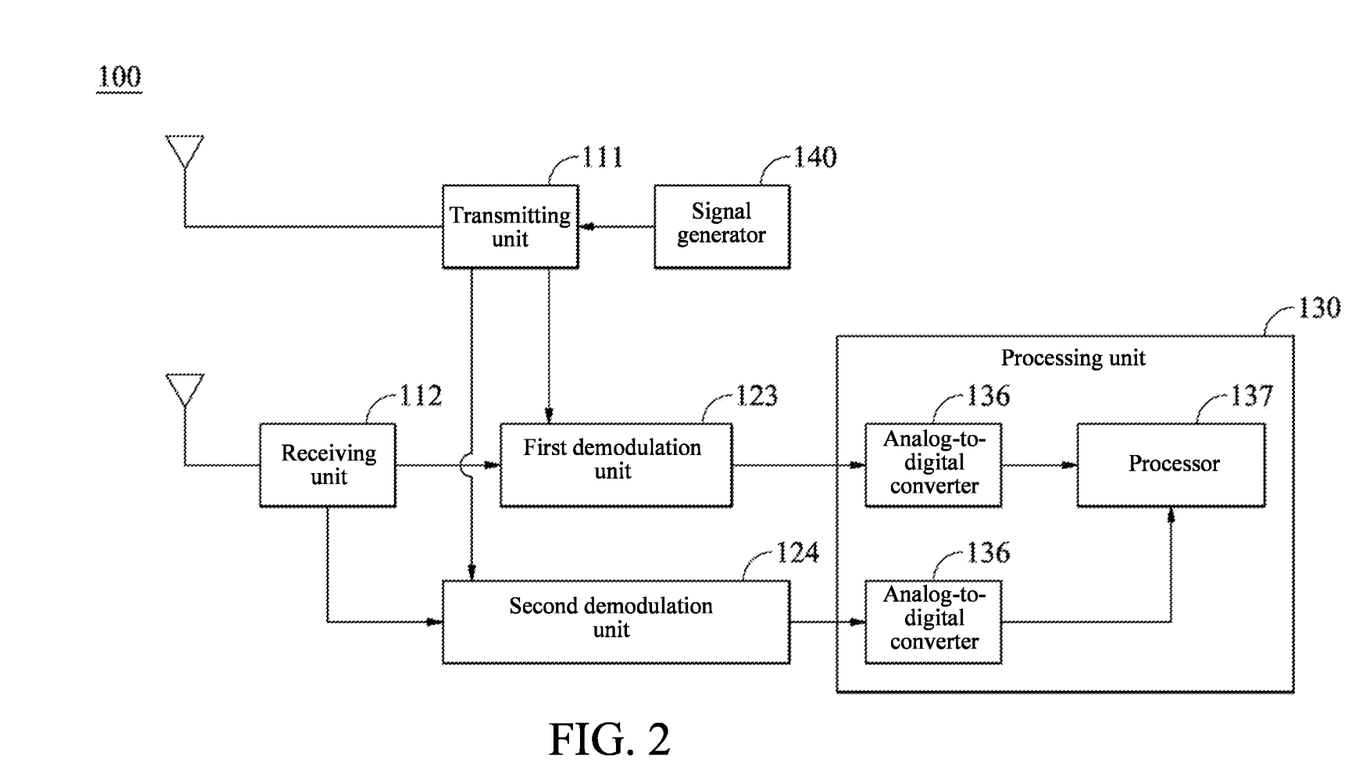
FIG. 2 is a schematic architectural diagram of an FMCW radar device according to some embodiments.
Figure 3:
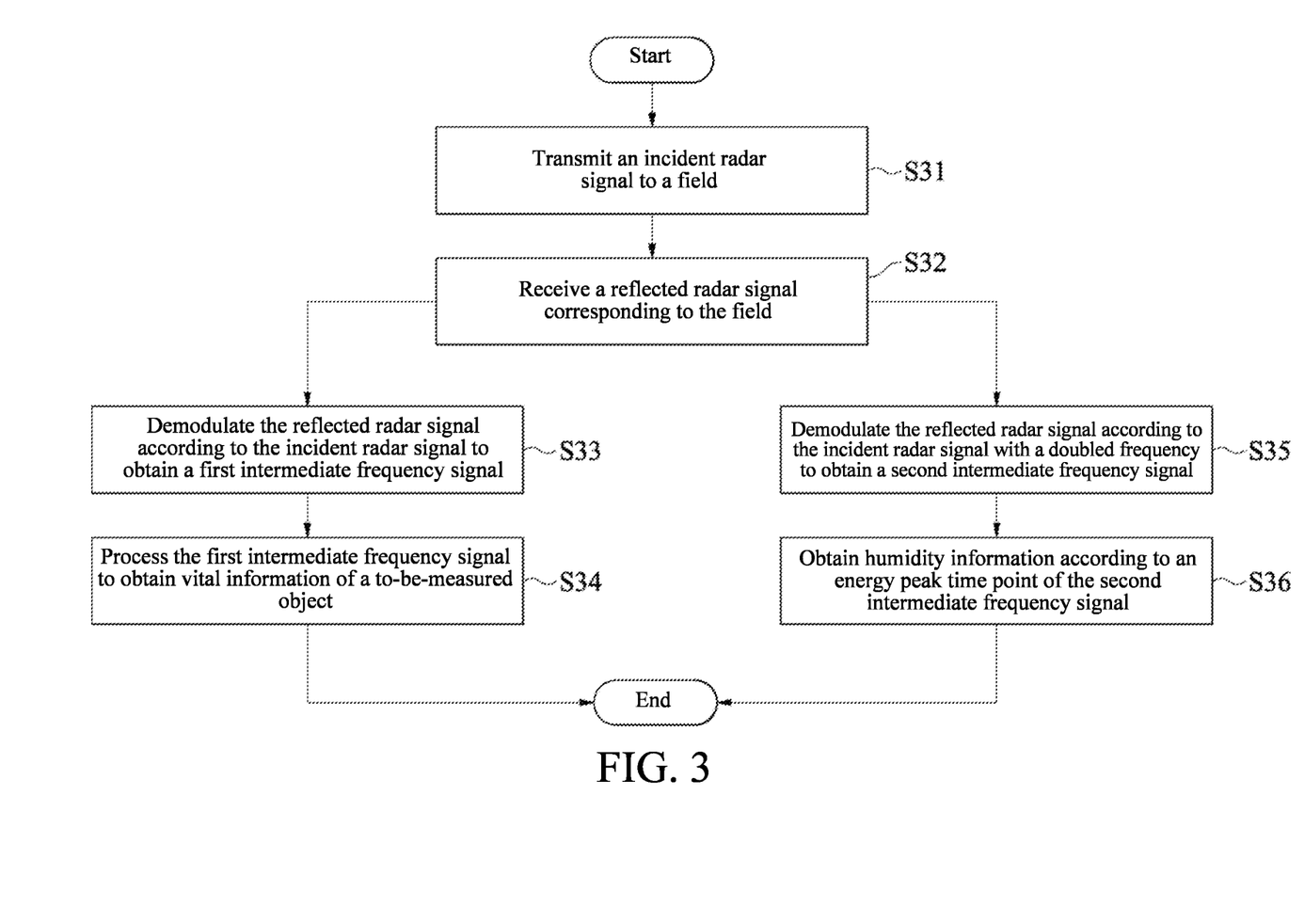
FIG. 3 is a flowchart of a method for detecting vital information and humidity according to some embodiments.
Figure 4:
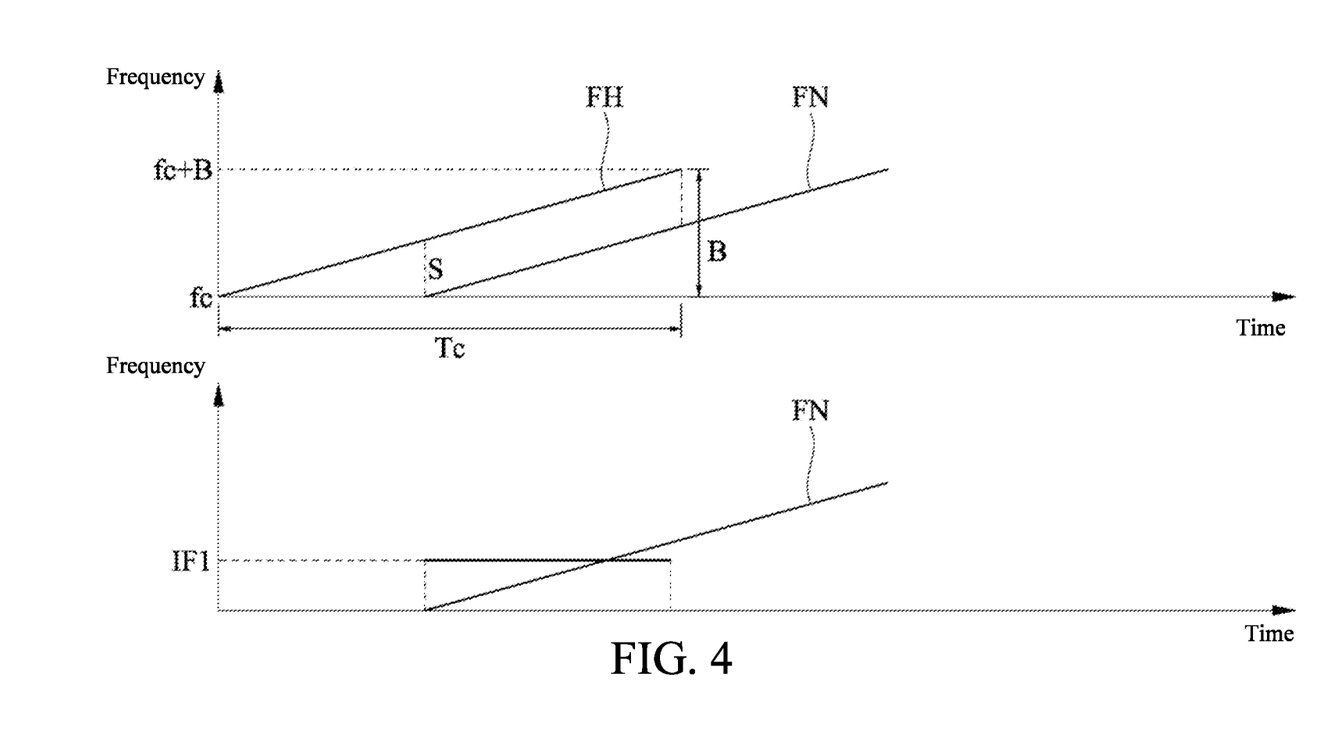
FIG. 4 is a schematic diagram of demodulating a first intermediate frequency signal according to an embodiment.

Reference can be made to both FIG. 2 and FIG. 3, FIG. 2 is a schematic architectural diagram of an FMCW radar device 100 according to some embodiments, and FIG. 3 is a flowchart of a method for detecting vital information and humidity according to some embodiments. The FMCW radar device 100 includes: a transmitting unit 111, a receiving unit 112, a first demodulation unit 123, a second demodulation unit 124, a processing unit 130 and a signal generator 140. The processing unit 130 is coupled to the transmitting unit 111, the receiving unit 112, the first demodulation unit 123, and the second demodulation unit 124 to control the units. The processing unit 130 includes two analog-to-digital converters 136 and a processor 137. The signal generator 140 generates a chirp signal (as shown in FIG. 4). The transmitting unit 111 is configured to transmit the incident radar signal FH (step S31). The transmitting unit 111 includes a transmitting antenna and a power amplifier (not shown in the figure). After the transmitting unit 111 receives the chirp signal generated by the signal generator 140, the chirp signal is amplified by the power amplifier and then is transmitted by an antenna. Therefore, the transmitting antenna needs to be designed to work effectively within a transmitting frequency range. The transmitting antenna may be a patch antenna, but the present disclosure is not limited thereto.

The receiving unit 112 is configured to receive the reflected radar signal FN and the reflected radar signal FN' (step S32). The receiving unit 112 includes a receiving antenna, and an operating frequency range of the receiving antenna needs to cover frequencies of the reflected radar signal FN and the reflected radar signal FN'. Optionally, when the operating frequency range of a receiving antenna can cover the frequencies of the reflected radar signal FN and the reflected radar signal FN', only one receiving antenna is required. Conversely, two receiving antennas may be used, and individually work in different frequency ranges, to respectively cover the frequencies of the reflected radar signal FN and the reflected radar signal FN'. It can be understood that, if only the reflected radar signal FN and the reflected radar signal FN' of the same frequency are received, there may be only one receiving antenna.

The first demodulation unit 123 and the second demodulation unit 124 are coupled to the transmitting unit 111 and the receiving unit 112, and are configured to respectively demodulate the reflected radar signal FN and the reflected radar signal FN' to respectively obtain a first intermediate frequency signal and a second intermediate frequency signal (step S33 and step S35). The two analog-to-digital converters 136 are respectively coupled to output ends of the first demodulation unit 123 and the second demodulation unit 124, and are coupled to the processor 137. After the two analog-to-digital converters 136 respectively convert the first intermediate frequency signal and the second intermediate frequency signal into digital signals, the processor 137 performs signal processing. Vital information of the to-be-measured object 900 can be obtained according to the first intermediate frequency signal (step S34). Humidity information can be obtained according to the second intermediate frequency signal (step S36). Therefore, the vital information and humidity information can be obtained through the FMCW radar device 100. For example, an application applied to baby care can learn of vital signs and a diaper status of a baby simultaneously, but the present invention is not limited to this application.

FIG. 4 is a schematic diagram of demodulating a first intermediate frequency signal according to an embodiment. Although only one chirp signal is displayed, the incident radar signal FH should include a plurality of chirp signals. A frequency of the chirp signal linearly increases with time from a modulation starting frequency fc to an end frequency after a time period Tc. A difference between the modulation starting frequency fc and the end frequency is a pulse bandwidth B. A modulation slope is S. In some embodiments, the modulation starting frequency fc is 24 GHz or 77 GHz, but the present disclosure is not limited thereto. After the incident radar signal FH is reflected, the receiving unit 112 receives the reflected radar signal FN, which can be regarded as a delayed version of the incident radar signal FH. The first demodulation unit 123 couples the incident radar signal FH and the reflected radar signal FN to obtain a coupled signal with a difference in frequency between the two, that is, an intermediate frequency signal. After the intermediate frequency signal is obtained, band-pass filtering can further be performed to filter out a high frequency signal. For the sake of distinction, an intermediate frequency signal obtained by demodulation through the first demodulation unit 123 is referred to as a first intermediate frequency signal. It can be seen that a frequency value IF1 of the first intermediate frequency signal is a specific value, and the frequency value IF1 varies with a time point at which the reflected radar signal FN is received. That is, the frequency value IF1 of the first intermediate frequency signal can reflect a distance between the FMCW radar device 100 and the to-be-measured object 900. Therefore, in step S34, the analog-to-digital converter 136 is configured to convert the first intermediate frequency signal into a digital signal. Then, the processor 137 performs a fast Fourier transform (referred to as a distance Fourier transform hereinafter) to the digital signal, to obtain distance information of the to-be-measured object 900. Next, a Doppler Fourier transform is performed by the processor 137 to obtain phase information, thereby obtaining the vital information of the to-be-measured object 900. Signal processing, such as noise removal, high frequency signal removal, and removal of unsuitable respiratory harmonics, can further be performed before the fast Fourier Transform is performed.

Figure 5:
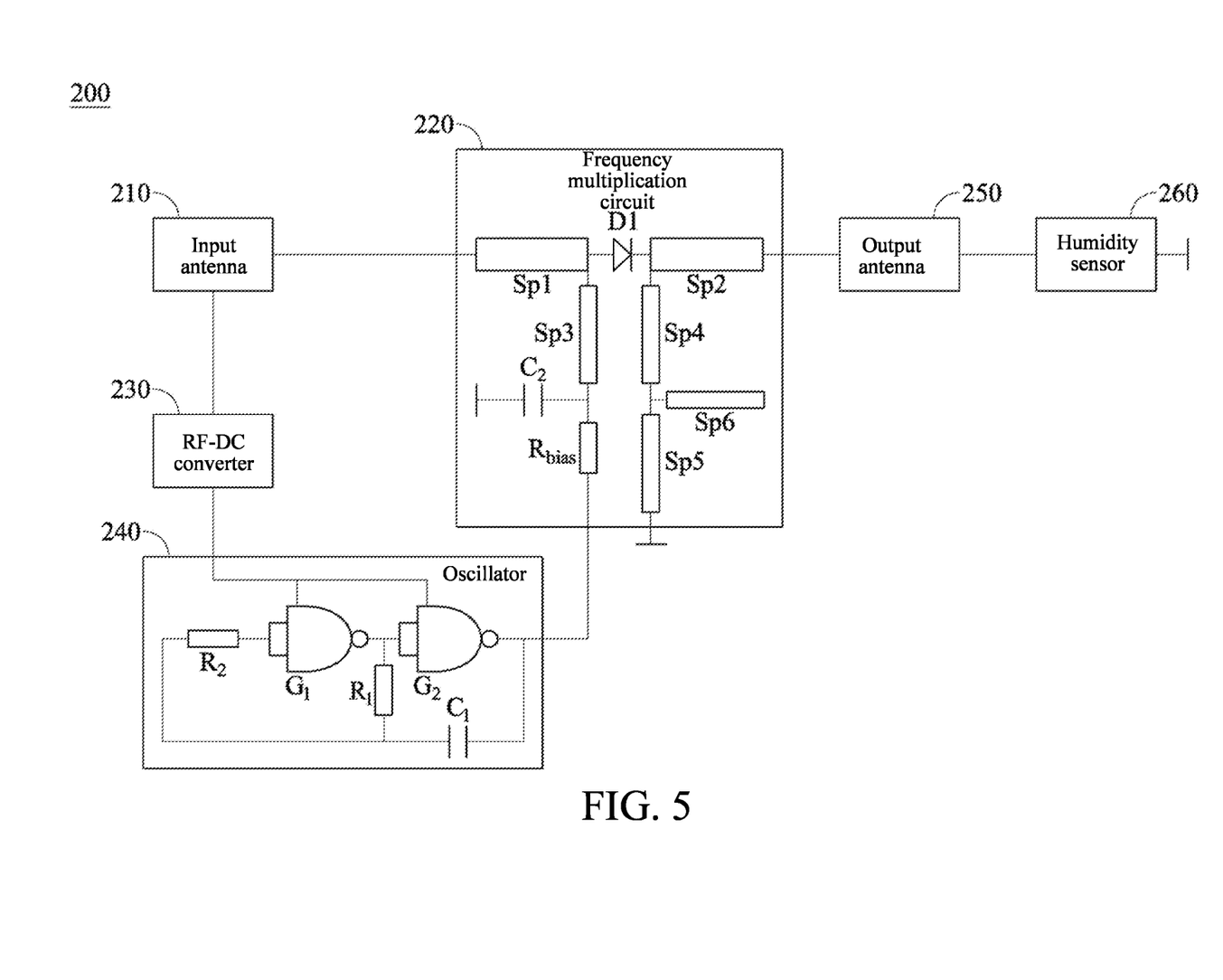
FIG. 5 is a schematic architectural diagram of a humidity sensor tag according to an embodiment.

Before the processing of the second intermediate frequency signal (that is, the intermediate frequency signal obtained by the second demodulation unit 124 through demodulation) is described, an architecture of the humidity sensor tag 200 is described first. FIG. 5 is a schematic architectural diagram of a humidity sensor tag 200 according to an embodiment. The humidity sensor tag 200 includes an input antenna 210, a frequency multiplication circuit 220, an RF-DC converter 230, an oscillator 240, an output antenna 250 and a humidity sensor 260.

The input antenna 210 is configured to receive the incident radar signal FH transmitted from the FMCW radar device 100. The input antenna 210 may be a double-dipole patch antenna, but the present disclosure is not limited thereto. The input antenna 210 is coupled to the frequency multiplication circuit 220 and the RF-DC converter 230. The frequency multiplication circuit 220 receives the incident radar signal FH received by the input antenna 210, and performs frequency multiplication on the incident radar signal FH, that is, generates a signal with a frequency of 2$f0$ (or frequency-multiplied signal) according to the incident radar signal FH (or baseband signal) with a frequency of f0. The RF-DC converter 230 is an energy collector, which collects energy of the incident radar signal FH received by the input antenna 210, and energy of some radio frequency signals is collected by the RF-DC converter 230 and boosted to an operating voltage of another circuit to provide an operating voltage for the humidity sensor tag 200. Therefore, the humidity sensor tag 200 does not need to be additionally equipped with a battery. However, in some embodiments, a battery may be installed in place of the RF-DC converter 230 to provide a circuit operating voltage. The RF-DC converter 230 is mainly implemented by a voltage multiplier including a plurality of diodes and a plurality of capacitors. The RF-DC converter 230 is further coupled to the oscillator 240 to supply the oscillator 240 with an operating voltage. The oscillator 240 is coupled to a bias end of the frequency multiplication circuit 220 to generate a specific frequency signal to modulate a signal of the frequency multiplication circuit 220. The specific frequency signal can be identified as a tag. FIG. 5 shows composition of the oscillator 240, which can be implemented by elements such as inverters G1, G2, resistors R1, R2, and a capacitor C1, but the present disclosure is not limited thereto.

FIG. 5 further shows composition of the frequency multiplication circuit 220, but the present disclosure is not limited thereto. The frequency multiplication circuit 220 includes a diode D1, a plurality of microstrip lines Sp1 to Sp6, a resistor $R_{bias}$, and a capacitor C2. An input end of the diode D1 is coupled to elements such as the microstrip lines Sp1, Sp3, the resistor $R_{bias}$, and the capacitor C2. The capacitor C2 is used as a bypass capacitor to filter out a frequency-multiplied signal (2$f0$). An output end of the frequency multiplication circuit 220 can be started or stopped by adjusting a bias voltage of the diode D1. The resistor $R_{bias}$ is used as a bias resistor and is coupled to the oscillator 240 to control and modulate the frequency multiplication circuit 220. An output end of the diode D1 is coupled to the microstrip lines Sp2, Sp4, Sp5, Sp6, which form a high-pass filter to filter out the baseband signal (f0). A length of the microstrip line Sp3 is a quarter wavelength of the baseband signal, and lengths of the microstrip lines Sp4, Sp5, Sp6 are a quarter wavelength of the frequency-multiplied signal.

The output antenna 250 is coupled to the frequency multiplication circuit 220 to transmit the modulated and frequency multiplied radio frequency signal, that is, the output is coupled as the frequency-multiplied signal (2$f0$) of a specific frequency signal identified by a tag. The output antenna 250 is coupled to the humidity sensor 260 to form a humidity detection antenna. The humidity sensor 260 is a variable capacitor. A change of a medium caused by humidity affects a dielectric coefficient of the capacitor, which in turn affects a resonance frequency of the output antenna 250. In this way, energy intensity of the frequency-multiplied signal (2$f0$) changes. Therefore, the FMCW radar device 100 can learn of a humidity change by detecting a change of signal strength of the frequency-multiplied signal (2$f0$). The humidity sensor 260 may be an interdigital capacitor or a parallel plate capacitor.

Figure 6:
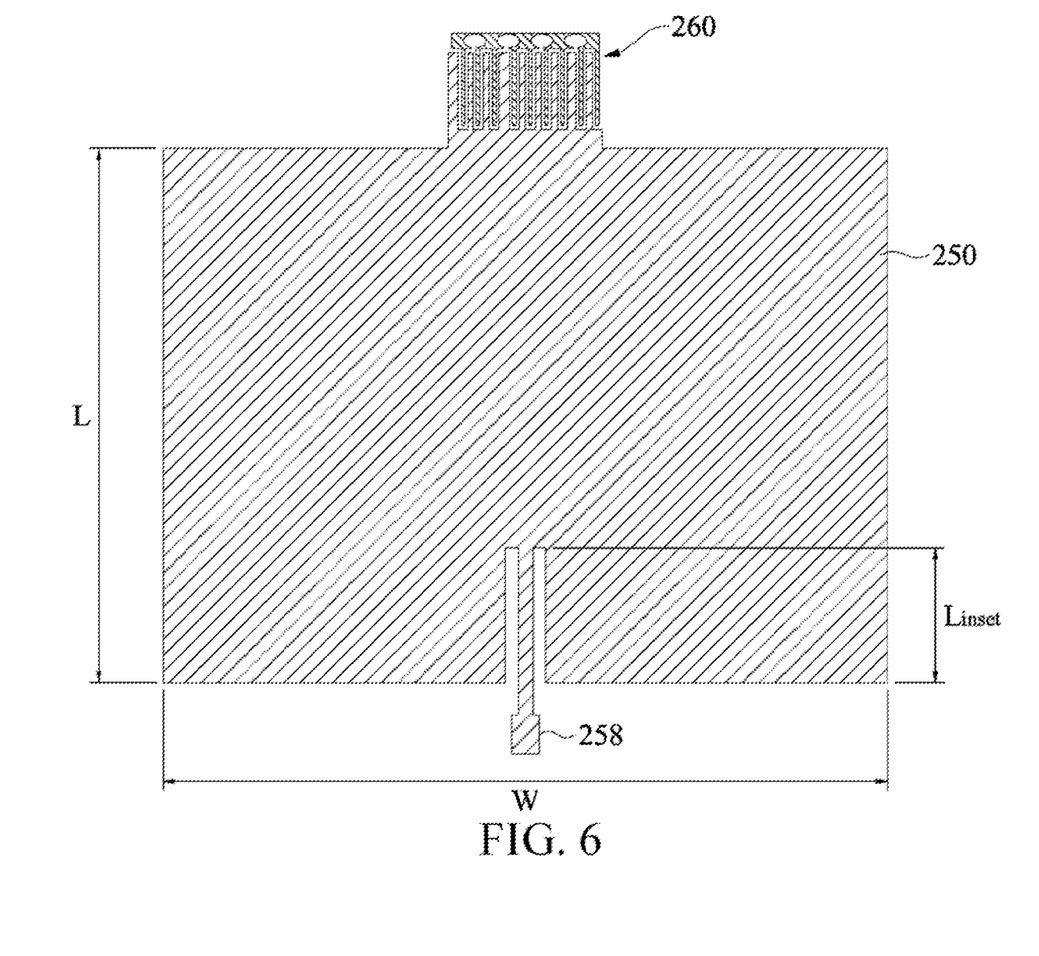
FIG. 6 is a schematic structural diagram of a humidity detection antenna according to an embodiment.

FIG. 6 is a schematic structural diagram of a humidity detection antenna according to an embodiment. A endpoint 258 is a signal feed-in end of the output antenna 250 and receives a signal of the frequency multiplication circuit 220. The output antenna 250 is a patch antenna herein, a length L is 37.5 cm, a width W is 51 cm, and a length of a feed section $L_{inset}$ is 9.5 cm. The humidity sensor 260 is an interdigital capacitor with 18 interdigitated electrodes staggered with each other. Each electrode has a length of 5 cm, a width of 0.6 cm, and a spacing of 0.3 cm. The foregoing specifications are only examples, and the present disclosure is not limited thereto.

Figure 7:
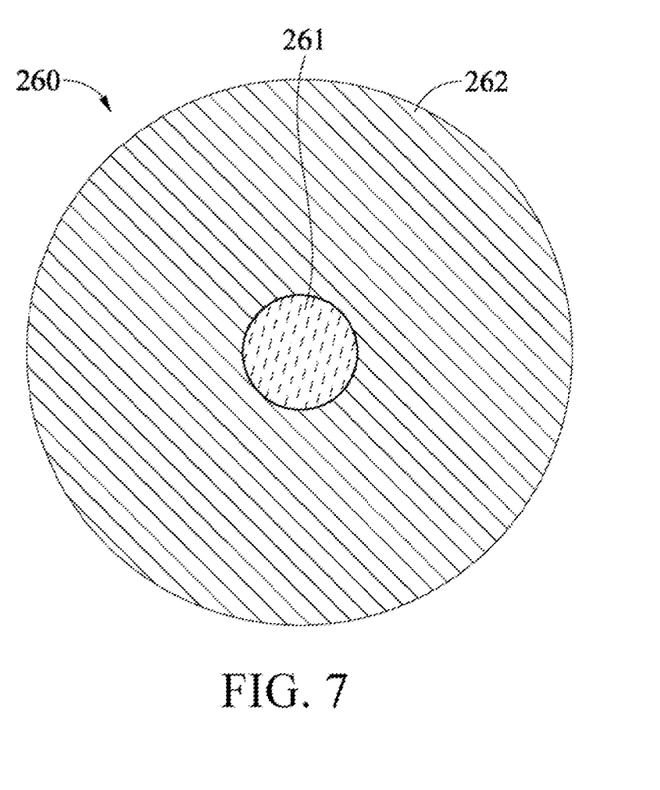
FIG. 7 is a schematic structural diagram of a humidity sensor according to an embodiment.

FIG. 7 is a schematic structural diagram of a humidity sensor 260 according to an embodiment. The humidity sensor 260 is a parallel plate capacitor with two parallel plates 261 and 262 spaced up and down.

Figure 8:
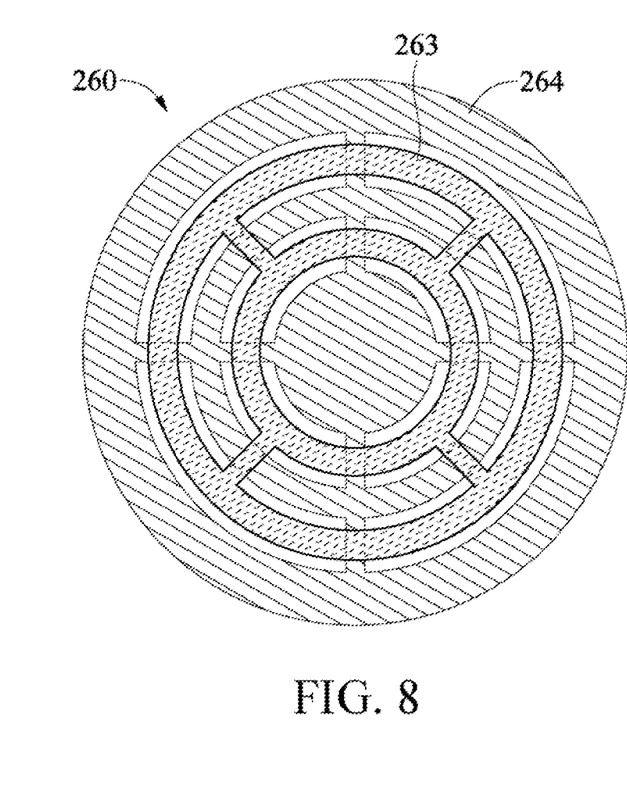
FIG. 8 is a schematic structural diagram of a humidity sensor according to another embodiment.

FIG. 8 is a schematic structural diagram of a humidity sensor 260 according to another embodiment. The humidity sensor 260 is a ring-shaped interdigital capacitor, and includes an upper ring 263 and a lower ring 264 disposed spaced apart in a ring-shaped staggered manner.

Referring to FIG. 2 and FIG. 3 again, the first demodulation unit 123 is configured to demodulate the reflected radar signal FN reflected by the to-be-measured object 900. Therefore, a frequency of the reflected radar signal FN is the same as a frequency of the incident radar signal FH, both of which are f0. The second demodulation unit 124 is configured to demodulate the reflected radar signal FN' backscattered by the humidity sensor tag 200. As described above, a frequency of the reflected radar signal FN' is 2$f0$. The second demodulation unit 124 is coupled to the transmitting unit 111 and the receiving unit 112, and is configured to receive the frequency multiplied incident radar signal FH (2$f0$) from the transmitting unit 111, and demodulate the reflected radar signal FN' according to a frequency-multiplied (2$f0$) corresponding to the incident radar signal FH to obtain the second intermediate frequency signal. The transmitting unit 111 includes a frequency multiplier to generate the frequency-multiplied signal 2$f0$ (step S35).

Next, step S36 is described, that is, how to use the second intermediate frequency signal to obtain the humidity information. Similar to the first demodulation unit 123, after the second demodulation unit 124 obtains the second intermediate frequency signal, band-pass filtering may further be performed to filter out a high frequency signal. Because frequency doubling is used for demodulation, a frequency-multiplied signal responded by the non-humidity sensor tag 200 is filtered and removed, and only a response signal of the humidity sensor tag 200 is retained, and information irrelevant to the humidity sensor tag 200 is not extracted.

Figure 9:
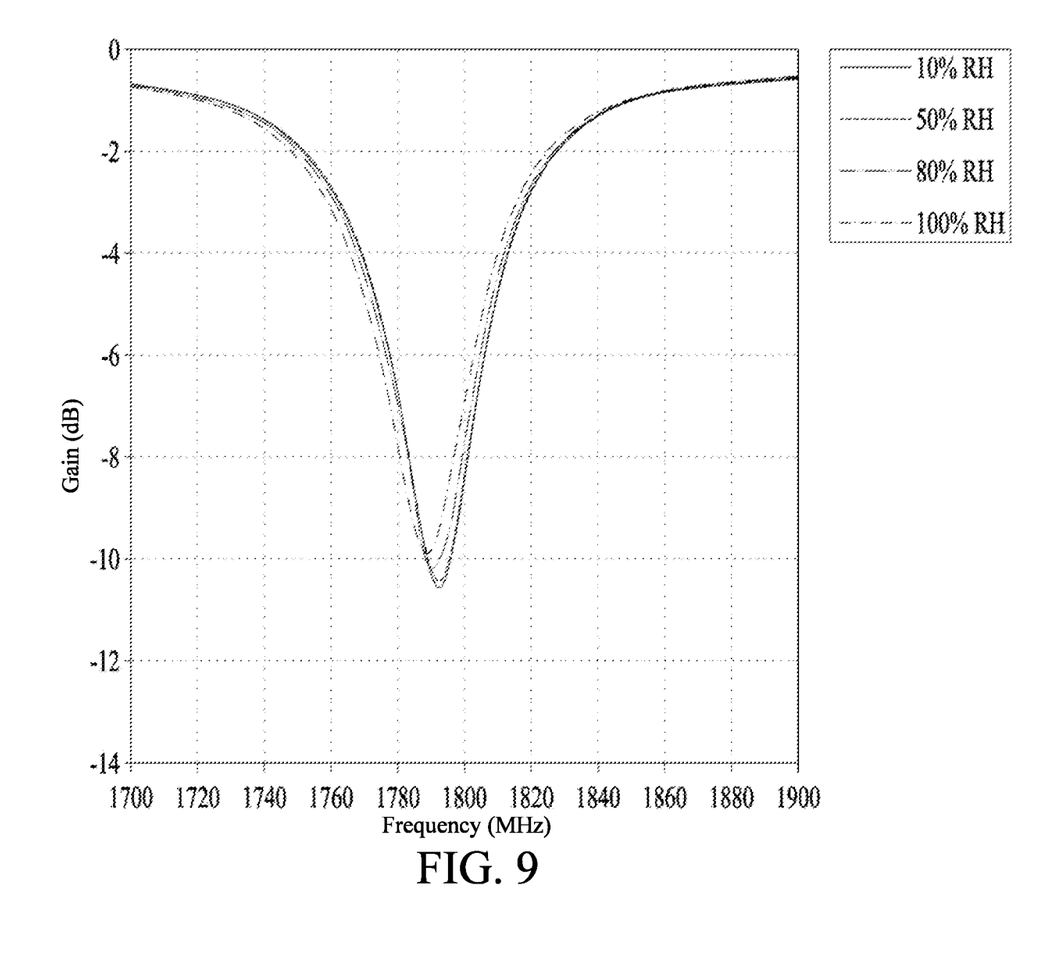
FIG. 9 is a frequency response diagram of the humidity detection antenna shown in FIG. 6 under different humidity environments.

FIG. 9 is a frequency response diagram of the humidity detection antenna shown in FIG. 6 under different humidity environments. It can be seen that when it is dry, because an antenna circuit of the humidity detection antenna is well coordinated, the strength of the reflected radar signal FN' is strong. When it is wet, because an antenna circuit of the humidity detection antenna is not well coordinated, the intensity of the reflected radar signal FN' is weak. However, regardless of humidity, the reflected radar signal FN' is the strongest at the resonance frequency. A resonance point is an energy peak position. A frequency of the resonance point varies with the humidity of the humidity detection antenna.

Figure 10:
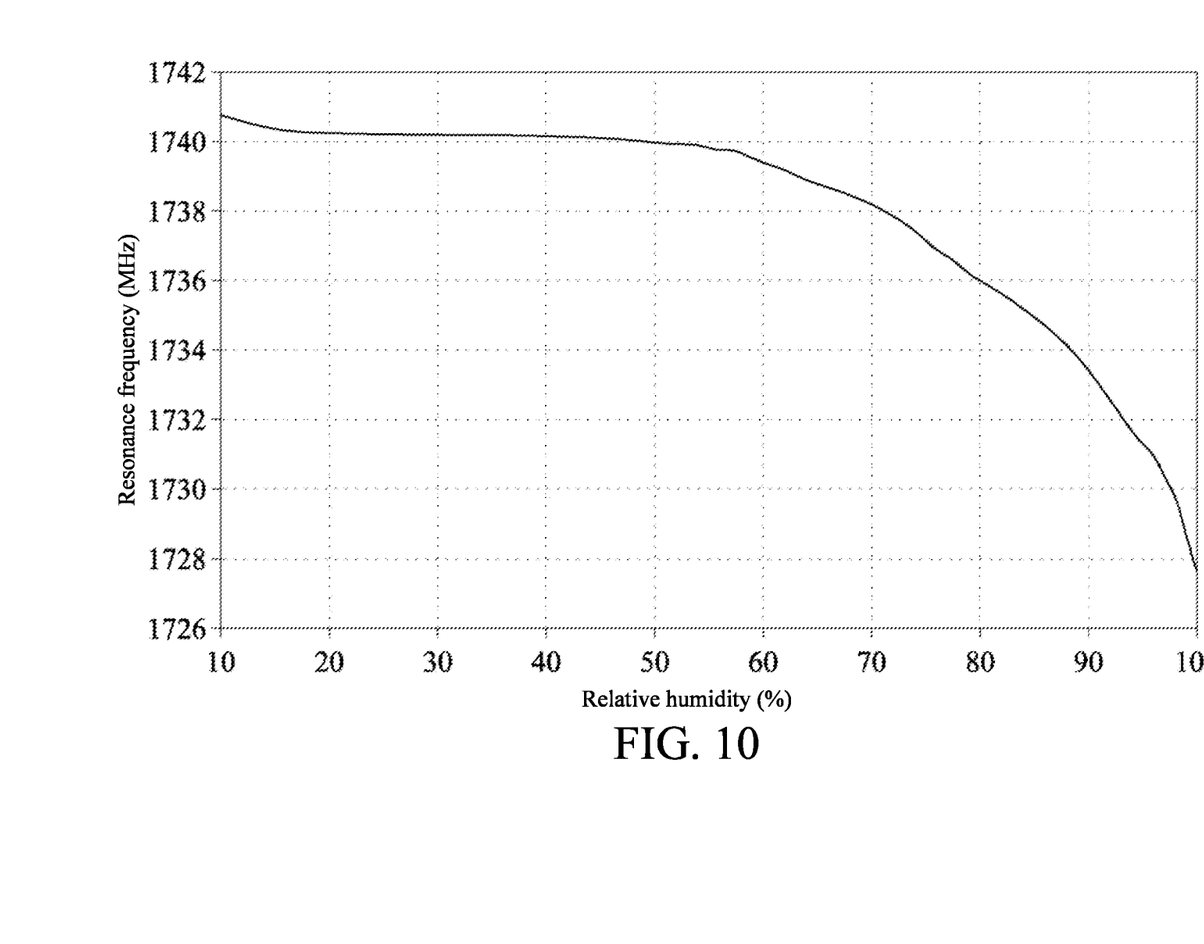
FIG. 10 is a diagram showing a relationship between a resonance frequency and relative humidity of the humidity detection antenna shown in FIG. 6.

FIG. 10 is a diagram showing a relationship between a resonance frequency and relative humidity of the humidity detection antenna shown in FIG. 6. After specific humidity is exceeded (such as more than 55%), the resonance frequency has a correspondence with the relative humidity. Therefore, if a current resonance frequency of the humidity detection antenna can be found, current humidity can be obtained through comparison.

Figure 11:
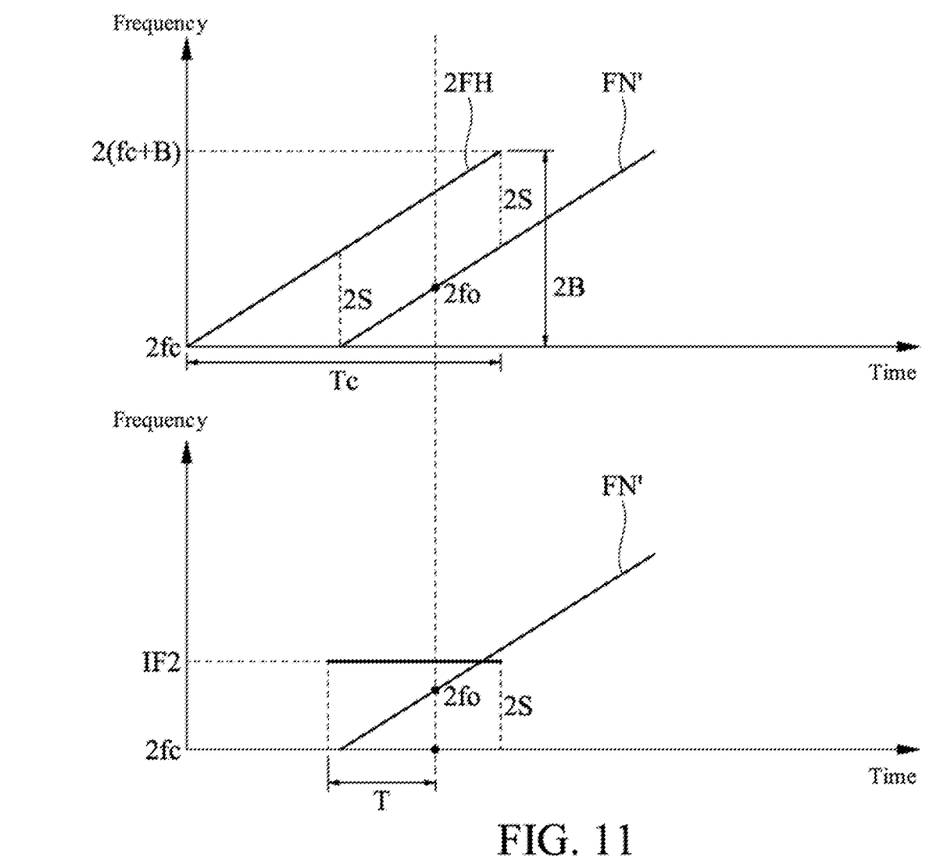
FIG. 11 is a schematic diagram of demodulating a second intermediate frequency signal according to an embodiment.

FIG. 11 is a schematic diagram of demodulating a second intermediate frequency signal according to an embodiment. Assuming that the to-be-searched-for resonance frequency is $2fo$, it can be found that by using a linear relationship, the resonance frequency $2fo$ can be inferred to be $2fc+T*2S$ provided that a time point of the resonance frequency $2fo$ is known. As described above, the resonance point is the energy peak position. Therefore, by analyzing an energy peak of the second intermediate frequency signal, the time point of the resonance frequency can be found, and a parameter T can be obtained. The parameter T is a period from a starting time of the reflected radar signal FN' to an energy peak time point. Accordingly, the resonance frequency $2fo$ can be obtained. Further, a relationship between the resonance frequency and the humidity shown in FIG. 10 is searched for by using the resonance frequency $2fo$, and the humidity information can be obtained. In some embodiments, the processor 137 may store lookup tables or functions for querying.

In some embodiments, the processor 137 may further perform a distance fast Fourier transform and a Doppler fast Fourier transform on the second intermediate frequency signal to obtain an identification signal of the humidity sensor tag 200 (a specific frequency generated by the oscillator 240 as a tag identification).

In some embodiments, the transmitting unit 111 can transmit two incident radar signals FH having a first frequency modulation frequency band and a second frequency modulation frequency band. In some embodiments, a frequency band commonly used by radars for measuring vital information, such as 24 GHz or 77 GHz, can be used as a frequency of the incident radar signal FH from which the first intermediate frequency signal can be obtained. Therefore, the detection sensitivity can be improved. On the other hand, a frequency band of 865 MHz to 868 MHz suitable for being used in the tag is used as a frequency of the incident radar signal FH from which the second intermediate frequency signal can be obtained. An antenna of the transmitting unit 111 includes a millimeter-wave antenna (for example, an Antipodal Vivaldi antenna) and an ultra-high frequency (UHF) band antenna.

Figure 12:
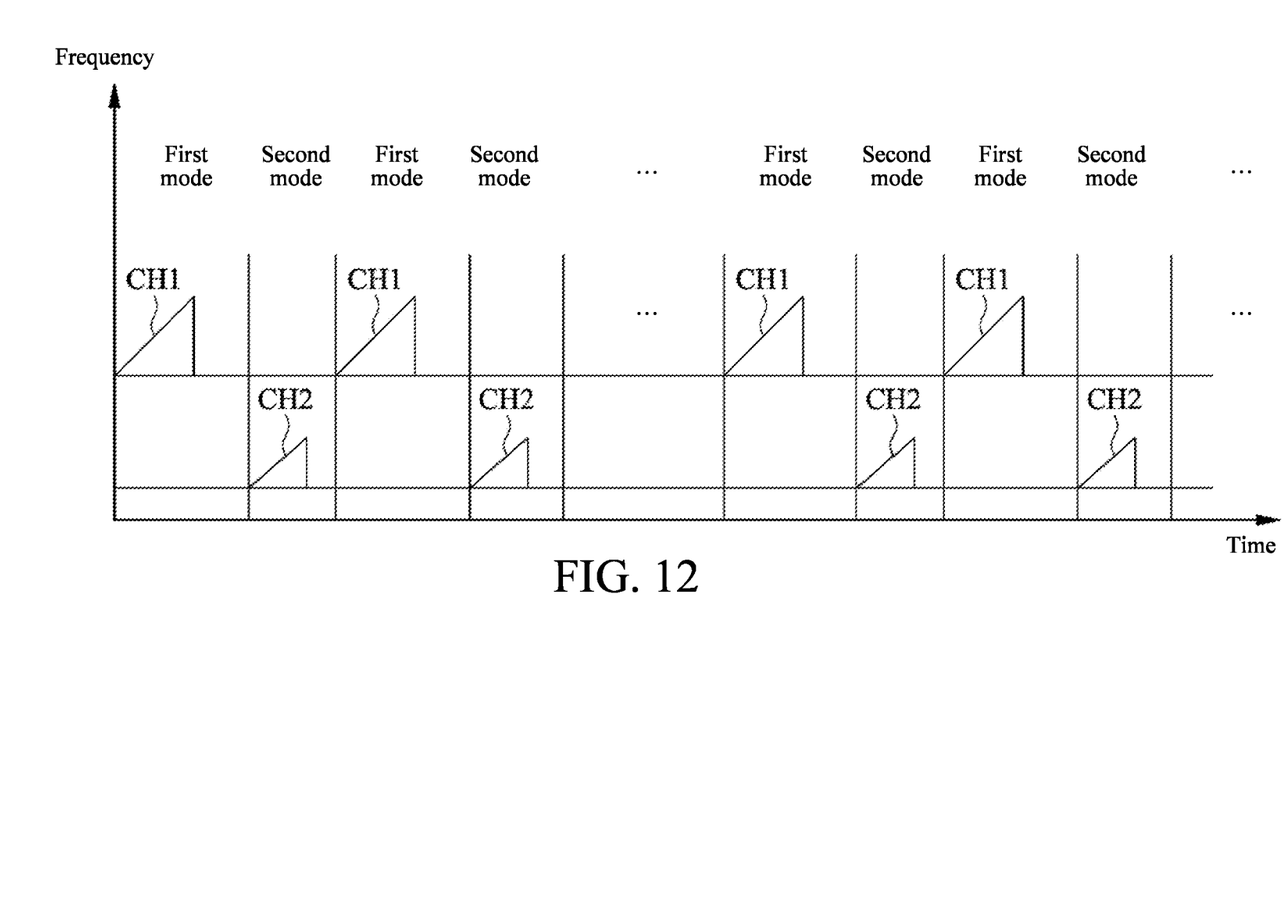
FIG. 12 is a schematic diagram of time-division multiplexing according to some embodiments.

FIG. 12 is a schematic diagram of time-division multiplexing according to some embodiments. The two incident radar signals FH of a third embodiment can be transmitted alternately in a time division duplex manner. In a first mode, the incident radar signal FH from which the first intermediate frequency signal can be obtained is transmitted, where the incident radar signal FH includes a plurality of chirp signals CH1. In a second mode, the incident radar signal FH from which the second intermediate frequency signal can be obtained is transmitted, where the incident radar signal FH includes a plurality of chirp signals CH2.

In some embodiments, the processor 137 is, for example, a central processing unit (CPU), a graphics processing unit (GPU), or another programmable general purpose or special purpose microprocessor, a digital signal processor (DSP), a programmable controller, an application-specific integrated circuit (ASIC), a programmable logic device (PLD), or another similar device, wafer, integrated circuit, or a combination thereof.

In summary, the FMCW radar device and the method for detecting vital information and humidity according to some embodiments can measure the vital information and humidity at the same time, thereby saving device space and the hardware costs.

What is claimed is:

1. A method for detecting vital information and humidity, comprising:

transmitting an incident radar signal to a field by a transmitting unit, and receiving a reflected radar signal corresponding to the field by a receiving unit, wherein the incident radar signal comprises a plurality of chirp signals;

demodulating the reflected radar signal according to the incident radar signal to obtain a first intermediate frequency signal by a first demodulation unit;

demodulating the reflected radar signal according to the frequency-multiplied incident radar signal to obtain a second intermediate frequency signal by a second demodulation unit;

processing the first intermediate frequency signal to obtain vital information of a to-be-measured object by a processing unit; and obtaining humidity information according to an energy peak time point of the second intermediate frequency signal by the processing unit.

2. The method for detecting vital information and humidity according to claim 1, wherein before the humidity information is obtained, a resonance frequency is obtained according to the energy peak time point, to obtain the humidity information according to the resonance frequency.

3. The method for detecting vital information and humidity according to claim 2, wherein the resonance frequency is $2fc+T*2S$, wherein fc is an initial frequency of the chirp signal, T is a period from a starting time of the reflected radar signal to the energy peak time point, and S is a modulation slope of the chirp signal.

4. The method for detecting vital information and humidity according to claim 2, wherein the humidity information is obtained by searching for a resonance frequency-humidity relationship according to the resonance frequency.

5. The method for detecting vital information and humidity according to claim 1, wherein the vital information is obtained by performing a distance fast Fourier transform and a Doppler fast Fourier transform on the first intermediate frequency signal.

6. The method for detecting vital information and humidity according to claim 1, further comprising:

obtaining an identification signal of a humidity sensor tag by performing a distance fast Fourier transform and a Doppler fast Fourier transform on the second intermediate frequency signal.

7. A frequency-modulated continuous wave (FMCW) radar device, comprising:

a transmitting unit, configured to transmit an incident radar signal to a field, wherein the incident radar signal comprises a plurality of chirp signals;

a receiving unit, configured to receive a reflected radar signal corresponding to the field;

a first demodulation unit, coupled to the transmitting unit and the receiving unit, and configured to obtain a first intermediate frequency signal according to the reflected radar signal and the incident radar signal through demodulation;

a second demodulation unit, coupled to the transmitting unit and the receiving unit, and configured to obtain a second intermediate frequency signal according to the reflected radar signal and the frequency-multiplied incident radar signal through demodulation; and a processing unit, coupled to the transmitting unit, the receiving unit, the first demodulation unit, and the second demodulation unit, and configured to process the first intermediate frequency signal to obtain vital information of a to-be-measured object, and obtain humidity information according to an energy peak time point of the second intermediate frequency signal.

8. A frequency-modulated continuous wave (FMCW) radar device, comprising:

a transmitting unit, configured to transmit two incident radar signals having a first frequency modulation frequency band and a second frequency modulation frequency band respectively to a field, wherein the two incident radar signals comprise a plurality of chirp signals;

a receiving unit, configured to receive a reflected radar signal corresponding to the field;

a first demodulation unit, coupled to the transmitting unit and the receiving unit, configured to receive the incident radar signal having the first frequency modulation frequency band, and obtain a first intermediate frequency signal according to the reflected radar signal and the incident radar signal having the first frequency modulation frequency band through demodulation;

a second demodulation unit, coupled to the transmitting unit and the receiving unit, configured to receive the incident radar signal having the second frequency modulation frequency band, and obtain a second intermediate frequency signal according to the reflected radar signal and the incident radar signal having the second frequency modulation frequency band through demodulation; and a processing unit, coupled to the transmitting unit, the receiving unit, and the demodulation unit, and configured to process the first intermediate frequency signal to obtain vital information of a to-be-measured object, and obtain humidity information according to an energy peak time point of the second intermediate frequency signal.

9. The FMCW radar device according to claim 8, wherein antennas of the transmitting unit are respectively a millimeter-wave antenna and an ultra-high frequency (UHF) band antenna.

10. The FMCW radar device according to claim 8, wherein the chirp signals of the two incident radar signals are transmitted alternately in a time division duplex manner.

* * * * *